United States Patent [19]

Blair

[11] Patent Number: 5,700,889

[45] Date of Patent: Dec. 23, 1997

[54] PROCESS FOR POLYMERIZATION OF COPOLYMERS OF TETRAFLUOROETHYLENE AND HEXAFLUOROPROPYLENE

[75] Inventor: Leslie Mitchell Blair, Parkersburg, W. Va.

[73] Assignee: E. I. Du Pont de Nemours and Company, Wilmington, Del.

[21] Appl. No.: 678,920

[22] Filed: Jul. 12, 1996

Related U.S. Application Data

[60] Provisional application Nos. 60/012,241, Feb. 26, 1996 and 60/002,405, Aug. 17, 1995.

[51] Int. Cl.$^6$ .................................................. C08F 16/24
[52] U.S. Cl. ............................................................ 526/247
[58] Field of Search .................................................. 526/247

[56] References Cited

U.S. PATENT DOCUMENTS 4,380,618  4/1983  Khan et al. .

FOREIGN PATENT DOCUMENTS 0075312  3/1983  European Pat. Off. ............ 526/247

*Primary Examiner*—Joseph L. Schofer
*Assistant Examiner*—N. Sarafim

[57] ABSTRACT

An aqueous polymerization process yields copolymers of tetrafluoroethylene and hexafluoropropylene that have low instability as polymerized and can by used without elaborate finishing steps.

12 Claims, No Drawings

PROCESS FOR POLYMERIZATION OF COPOLYMERS OF TETRAFLUOROETHYLENE AND HEXAFLUOROPROPYLENE

RELATED APPLICATIONS

This application is a continuation of provisional application 60/012,241, filed Feb. 23, 1996 and a continuation-in-part of provisional application 60/002,405 filed Aug. 17, 1995.

FIELD OF THE INVENTION

This invention is in the field of melt-fabricable copolymers of tetrafluoroethylene and hexafluoropropylene.

BACKGROUND OF THE INVENTION

Melt-fabricable copolymers of tetrafluoroethylene (TFE) and hexafluoropropylene (HFP) are well known, as are polymerization processes for making them. Bro & Sandt in often-cited U.S. Pat. No. 2,946,763 disclose an aqueous process using water-soluble free-radical initiator. As disclosed therein, high levels of HFP incorporation are extremely difficult, a consequence of the low reactivity of HFP relative to the highly reactive TFE. A common approach to enhance reactivity of HFP is to carry out the polymerization at a temperature that is as high as possible, e.g., near and even above 100° C. Considerations with respect to polymerization temperature for TFE/HFP copolymers are reviewed, for example, by Morgan in U.S. Pat. No. 5,266,639.

As a consequence of the initiators used, TFE/HFP copolymers made by aqueous processes such as that of Bro & Sandt have unstable end groups, notably —COOH or salts thereof, that can decompose during subsequent processing and result in unacceptable bubbling in finished products. Various processes for stabilizing the end groups of such polymers have been devised. Schreyer, for example, in U.S. Pat. No. 3,085,083 discloses a humid heat treatment process for improving the stability of such polymers by converting unstable carboxylate end groups to relatively stable —CF$_2$H (hydride) end groups.

A second source of instability in TFE/HFP copolymers is believed to be a backbone instability attributed to the presence of HFP diads. Morgan & Sloan in U.S. Pat. No. 4,626,587 disclose a high-shear thermo-mechanical process for reducing the backbone instability in TFE/HFP copolymers. It is disclosed that, if the polymer contains unstable end groups or has poor color after removal from the high-shear extruder, such problems can be eliminated by fluorination (contact with elemental fluorine). TFE/HFP copolymer made by the polymerization process of Bro & Sandt and stabilized by high-shear extrusion generally does require an after-treatment. Such polymer finishing steps are time-consuming and costly.

The use of certain chain transfer agents in aqueous polymerization of dipolymers of TFE and PAVE to control die swell, in turn attributed to control of molecular weight distribution, is disclosed by Gresham & Vogelpohl in U.S. Pat. No. 3,635,926. However, the use of chain transfer agent has a repressive effect on polymerization rate. This is particularly undesirable in copolymerization of TFE and HFP, for which the low reactivity of HFP itself has unfavorable impact on reaction rate.

It is common in the field to base HFP content of TFE/HFP copolymers on measurement of HFPI. This quantity was introduced by Bro & Sandt in U.S. Pat. No. 2,946,763 who also introduced the multiplicative factor 4.5 to obtain HFP content in wt % from HFPI. While recent calibrations have led to different multiplicative factors, HFPI values deduced from infrared measurements at different times are generally regarded as reliable.

The problem remains to make, by an aqueous process, TFE/HFP copolymer that is sufficiently stable to permit commercial use without a costly stabilization finishing procedure. Such copolymer should have total unstable fraction, as defined hereinbelow, of no more than 0.2%.

SUMMARY OF THE INVENTION

This invention is concerned with the process of copolymerizing tetrafluoroethylene with hexafluoropropylene in an aqueous medium in the presence of water soluble initiator and dispersing agent to obtain a partially-crystalline copolymer of tetrafluoroethylene and hexafluoropropylene which has a total unstable fraction of at least 0.3%. In accordance with the improvement in this process to reduce the total unstable fraction to be no more than 0.2%, the copolymerizing is carried out with chain transfer agent present, and with said initiator present in an amount effective to initiate no more than half of said copolymer molecules made.

In accordance with a further improvement in this process of copolymerizing tetrafluoroethylene with hexafluoropropylene, the amount of hexafluoropropylene present is reduced so as to counteract the reduction in copolymerization rate caused by the level of chain transfer agent used, and fluorinated vinyl ether is added to the aqueous medium for copolymerization with tetrafluoroethylene and hexafluoropropylene to compensate for the loss of toughness of the copolymer caused by the reduction in hexafluoropropylene, if reduced hexafluoropropylene were the only change made to the copolymerization. The resultant partially-crystalline copolymer comprises tetrafluoroethylene, hexafluoropropylene in an amount corresponding to HFPI of from 2.0 to 5.0, and from 0.2% to 4% by weight of at least one fluorinated vinyl ether.

DETAILED DESCRIPTION OF THE INVENTION

It has been discovered that TFE/HFP copolymers suitable for use in melt processing without a special stabilization process step can be made by aqueous polymerization using water soluble free-radical initiator to initiate the formation of only a relatively small fraction of the polymer molecules made, and high concentration of chain transfer agent (CTA) so that chain transfer initiates the formation of a relatively large fraction of the polymer molecules made The proportion of polymer molecules initiated by initiator and by chain transfer are small and large, respectively, relative to past polymerization practice. To achieve acceptable reaction rate despite the use of a high concentration of CTA, the concentration of HFP in polymerization, and therefore the amount of HFP in the copolymer, is reduced. To achieve satisfactory toughness, the HFP reduction is offset by a smaller increase in the amount of fluorinated vinyl ether (FVE) in the copolymer. To achieve satisfactory molecular weight in the presence of CTA, initiator concentration is reduced relative to that required in the absence of CTA. The combined use of increased CTA and reduced initiator results in a TFE/HFP copolymer having improved total stability, i.e., the combination of reduced backbone instability and a reduced —COOH end group population.

The TFE/HFP/FVE copolymers made by the process of this invention have HFP content corresponding to HFPI=

2.0–5.0, preferably HFPI=2.0–4.1. For reasons of productivity in polymerization, HFP content corresponding to HFPI=2.0–3.5 is especially preferred. HFPI is determined by an infrared method outlined below.

FVE content of the copolymers made by the process of this invention is in the range 0.2–4 wt %, preferably 0.4–2 wt %. Vinyl ethers that can be used in the process of this invention include those of the formula $CF_2=CFOR$ or $CF_2=CF-OR'-OR$ wherein —R and —R'— are independently completely-fluorinated or partially-fluorinated linear or branched alkyl and alkylene groups containing 1–8 carbon atoms. Preferred —R groups contain 1–4 carbon atoms, while preferred —R'— groups contain 2–4 carbon atoms. FVE of the formula $CF_2=CFOR$ are preferred, particularly perfluoro(alkyl vinyl ether) (PAVE). Preferred PAVE include perfluoro(methyl vinyl ether) (PMVE), perfluoro(ethyl vinyl ether) (PEVE), and perfluoro(propyl vinyl ether) (PPVE). PEVE is especially preferred.

One skilled in the art will recognize that one or more additional copolymerizable monomers can be incorporated in the TFE/HFP/FVE copolymers made by the process of this invention. The amount of such additional monomer will be such that the resultant copolymer remains partially crystalline, as indicated by detection of a melting endotherm by differential scanning calorimetry for resin as-polymerized, i.e., for resin that has not been previously melted.

Copolymers made by the process of this invention generally have melt viscosity (MV) in the range $0.5-50 \times 10^3$ Pa·s. MV in the range $1-10 \times 10^3$ Pa·s is preferred.

The polymerization process of this invention is an aqueous dispersion polymerization process. As is well known, such processes can be carried out in the presence of organic liquids, usually halogenated compounds. However, in light of current environmental concerns, polymerization in the absence of such compounds, i.e., solvent-free aqueous dispersion polymerization, is preferred.

The process of this invention differs from known aqueous processes for polymerizing TFE/HFP copolymers in that it employs an unusually large amount of chain transfer agent (CTA) and an unusually low amount of initiator relative to the mount of polymer made. The amounts of CTA and initiator are not independent, but are coupled, i.e., chain transfer and initiator complement one another in initiating the total quantity of polymer molecules made. For chosen CTA and initiator, the selection of the amount of one determines the amount of the other to be used in the process of this invention to make a copolymer of chosen composition and chosen molecular weight. Thus, the coupled amounts can be expressed in terms of the amount of initiator used to make a mole of copolymer.

Initiators commonly employed in emulsion (dispersion) polymerization of TFE copolymers are water-soluble free-radical initiators such as ammonium persulfate (APS), potassium persulfate (KPS), or disuccinic acid peroxide, or redox systems such as those based on potassium permanganate. Such initiators can be used in the process of this invention. APS and/or KPS is preferred. The amount of initiator employed depends on the effective amount of CTA used. Because of the interaction between chain transfer effect and initiator effect, the combined effect can be described in terms of the initiator. It will be understood that initiator efficiencies vary, so that the amount of initiator required to achieve reduced —COOH end group population will vary with the initiator. However, for APS and KPS for which initiation efficiency approaches 100% at high temperature (e.g. 100° C.), the amount of initiator, relative to the amount of polymer formed, is generally less than 0.5 mol/mol, desirably no more than 0.35 mol/mol, and preferably no more than 0.2 mol/mol. When the initiator has lower initiation efficiency, such as APS or KPS at lower temperature, these initiator amounts refer to the proportion of polymer molecules initiated (made) by the initiator. Both situations can be described in terms of effective initiator amount per mole of polymer made. Generally, there will be a reduction in the number of —COOH end groups due to initiation commensurate with the initiator reduction, relative to a copolymer of the same MV made in the absence of CTA.

There can also be a contribution to the population of —COOH end groups from rearrangement of the FVE (forming —COF ends that hydrolyze in aqueous media to —COOH ends), which rearrangement terminates a growing molecule. The contribution of FVE rearrangement to the —COOH population will depend at least on FVE type, FVE concentration, and reaction temperature. It is the combined contributions of the rearranging FVE and the CTA that constitute the chain transfer occurring in the polymerization reaction to complement initiation by the water soluble initiator, i.e., by initiating formation of the molecules not initiated by initiator. The contribution of FVE rearrangement to the —COOH population can be offset by buffering the polymerization with buffering agent such as ammonium carbonate or ammonia (ammonium hydroxide). As disclosed in U.S. Pat. No. 3,635,926, such buffering results in amide end groups.

A wide range of compounds can be used as CTA in the process of this invention. Such compounds include, for example, hydrogen-containing compounds such as hydrogen itself, the lower alkanes, and lower alkanes partially substituted with halogen atoms. The chain transfer activity of such compounds when used in TFE/HFP polymerization can result in copolymer having —$CF_2H$ end groups which are relatively stable. The CTA can contribute other relatively stable end groups, depending on the identity of the CTA. Preferred CTA include methane, ethane, and substituted hydrocarbons such as methyl chloride, methylene chloride, chloroform, and carbon tetrachloride. The molar amount of CTA used to achieve desired molecular weight will depend on the amount of initiator used and on the chain transfer efficiency of the chosen CTA. Chain transfer efficiency can vary substantially from compound to compound. The amount of CTA used will also depend on the type and concentration of FVE used in the TFE/HFP polymerization process of this invention, because the rearrangement of FVE that can occur also causes chain transfer.

Another effect of chain transfer, whether by CTA or by FVE, is related to the termination of the growing molecule that is inherent in chain transfer. When a molecule is terminated by chain transfer, it cannot be terminated by coupling and so cannot participate in formation of an HFP diad, the historically presumed source of backbone instability. Thus, the large concentration of CTA used in the process of this invention leads to reduced backbone instability as well as reduced —COOH end groups due to initiation.

The total stability, or instability, of the TFE/HFP copolymer made by the polymerization process of this invention can be characterized by weight loss as a result of controlled high temperature exposure. One method is total weight loss across a humid heat treatment (HHT) cycle. The HHT described below is similar to that disclosed by Schreyer (U.S. Pat. No. 3,085,083). A second method designed to measure total unstable fraction (TUF) involves, as also described below, the difference between weight losses measured after exposure for different times at high temperature in dry nitrogen. The high temperature exposure of the TUF method is easier to control, and TUF is used herein to characterize the effect of this invention. TUF for TFE/HFP copolymer made by the process of this invention is no more than 0.2%, preferably no more than 0.1%. The CTA contributes to reduced TUF in two ways, as described above, by providing relatively stable end groups and reducing backbone instability.

A broad range of temperatures can be used. Because of the low reactivity of HFP relative to that of TFE, higher temperatures are advantageous, such as temperatures in the range of about 95°–115° C. Temperature in the range 98°–108° C. is preferred for making the copolymers of this invention by the aqueous semibatch process used in the examples below. Surfactants used in emulsion polymerization appear to be less effective at temperatures above 103°–108° C. and there is a tendency to lose dispersion stability.

Surfactants suitable for use in dispersion polymerization of TFE/HFP copolymers can be used. Such surfactants include, for example, ammonium perfluorooctanoate (C-8), ammonium perfluorononanoate (C-9), and the perfluoroalkyl ethane sulfonic acids and salts thereof disclosed in U.S. Pat. No. 4,380,618.

After the reactor is charged with water, surfactant and monomers, heated to the chosen temperature, and agitation is started, a solution of initiator is added at a prescribed rate to initiate polymerization. A pressure drop is the usual indicator that polymerization has started. Then, TFE addition is started and controlled according to the scheme chosen to regulate the polymerization. An initiator solution, which can be the same as or different from the first initiator solution, is usually added throughout the reaction.

There are several alternatives for regulating the rate of TFE/HFP copolymerization, and these are applicable for the process of this invention. It is common with most alternatives first to precharge all HFP monomer and then to add TFE to the desired total pressure. Additional TFE is then added after initiator injection and reaction kickoff to maintain the chosen pressure. The TFE may be added at a constant rate, with agitator speed changed as necessary to increase or decrease actual polymerization rate and thus to maintain constant total pressure. Alternatively, the total pressure and the agitator speed may both be held constant, with TFE added as necessary to maintain the constant pressure. A third alternative is to carry out the polymerization in stages with variable agitator speed, but with steadily increasing TFE feed rates.

The HFP monomer is much less reactive than the TFE monomer so that the HFP/TFE ratio must be kept high to assure the desired incorporation of HFP, though not as high as required to achieve equivalent toughness in the absence of FVE, or as high as possible at comparable reaction rate in the absence of CTA.

Heretofore, FVE has been introduced into TFE/HFP copolymerization in order to improve properties for certain usage. In the present invention, the FVE is increased primarily to restore properties lost by reducing the HFP content, which is done to restore reaction rate lost by the CTA addition. The FVE can be introduced into the process either by pre-charge, pre-charge plus subsequent addition (pumping), or pumping of the FVE into the reactor. When FVE is PAVE, the reactivity of PAVE relative to TFE is such that TFE/HFP copolymer that is satisfactorily uniform with respect to PAVE incorporation can be obtained if PAVE is precharged to the reactor.

The TFE/HFP copolymer made by the polymerization process of this invention can be used for many purposes without special stabilization finishing steps. Finishing can be accomplished within the routine extrusion steps used to convert the solids isolated from the dispersion product of polymerization into the cubes (pellets) used in commerce normally suffices. Such pelletizing can be done with extrusion equipment known in the art, including twin screw and single screw extruders.

EXAMPLES

Fluoropolymer compositions were determined on 0.095–0.105 mm thick films pressed at 300° C., using Fourier transform infrared (FTIR) spectroscopy. For HFP determination, the method described in U.S. Pat. No. 4,380,618 was used. In applying this method, the absorbances of bands found at about 10.18 micrometers and at about 4.25 micrometers were used. HFP content is expressed as an HFP index (HFPI), the ratio of the 10.18 micrometers absorbance to the 4.25 micrometers absorbance. HFP content in wt % was calculated as 3.2×HFPI.

PEVE was determined from an infrared band at 9.17 micrometers using FTIR spectroscopy. PEVE content in wt % was calculated as 1.3×the ratio of the 9.17 micrometers absorbance to 4.25 micrometers absorbance. The absorbance at 9.17 micrometers was determined using a TFE/HFP dipolymer reference film to subtract out a strong absorbance that overlies the 9.17 micrometers band. The 4.25 micrometers internal thickness absorbance was determined without use of reference film.

End group analysis was also done by FTIR spectroscopy in a modification of the method disclosed in U.S. Pat. No. 3,085,083, using films 100 mm thick prepared by pressing at room temperature. The absorbance at 3557 cm$^{-1}$ was used to determine the population of —COOH end groups, while the absorbance at 1774 cm$^{-1}$ relative to the absorbance at 1813 cm$^{-1}$ was used to determine the population of hydrogen-bonded —COOH groups, also called —COOH dimers. When reported herein, the total measured population of —COOH is given, i.e., the sum of singlets and dimers.

Melt viscosities of the fluoropolymers were determined by ASTM method D1238-52T modified as described in U.S. Pat. No. 4,380,618.

Thermal characteristics of fluoropolymer resins were determined by DSC by the method of ASTM D-4591-87. The melting temperature reported is the peak temperature of the endotherm on second melting.

Average size of polymer particles as polymerized, i.e., raw dispersion particle size (RDPS), was measured by photon correlation spectroscopy.

The standard MIT folding endurance tester described in ASTM D-2176 was used for determining flex life (MIT Flex Life). Measurements were made using compression-molded films that were quenched in cold water. Film thickness was approximately 0.008±0.005 inch (0.20±0.013 mm).

In the following, unless otherwise stated, stated solution concentrations are based on combined weight of solvent water and of solute(s). Stated concentrations of polymer solids in dispersions are based on combined weights of solids and aqueous medium, and were determined gravimetrically, i.e., by weighing dispersion, drying, and weighing dried solids, or by an established correlation of dispersion specific gravity with the gravimetric method.

Total unstable fraction (TUF) was used as a measure of polymer instability. A weighed sample of copolymer resin was heated at 360° C. in a nitrogen atmosphere, and weight losses $\Delta W_1$ and $\Delta W_2$ were measured after 1 hr and after 2 hr, respectively. Then, TUF was calculated as TUF=$2\Delta W_1 - \Delta W_2$ and expressed relative to original weight (i.e., in %). The difference was taken to separate the effects of unstable entities, judged to occur in relatively short time (less than 1 hr), from background degradation occurring at the high temperature employed. TUF is interpreted as the sum of weight loss due to unstable end groups and of weight loss due to backbone unstable fraction, commonly attributed to HFP diads.

As indicated in the examples below, samples of raw polymer were subjected to a humid heat treatment (HHT) stabilization process consisting of heating at 360° C. for 1.5 hr in humid air containing 13 mol % water. Weight loss across HHT is a measure of the stability of the raw polymer.

For use in determining the molar quantity of copolymer produced in a given polymerization, number average molecular weight ($M_n$) was calculated from melt viscosity (MV) in Pa·s using the relationship $M_n = 10570 \times (MV)^{0.29}$. The total amount of copolymer produced was calculated from the amount of TFE added to the reactor during polymerization and the amounts of comonomer units in the copolymer as determined by infrared analysis.

Example 1

A cylindrical, horizontal, water-jacketed, paddle-stirred, stainless steel reactor having a length to diameter ratio of about 1.5 and a water capacity of 80 parts by weight was charged with 50 parts of demineralized water and 0.66 part of a 20 wt % solution of ammonium perfluorooctanoate surfactant (C-8, Fluorad® FC-143, 3M) in water. With the reactor paddle agitated at 35 rpm, the reactor was heated to 65° C., evacuated, purged with TFE, evacuated again, and 0.0046 part (calculated from 102 mmHg pressure rise) of ethane was introduced. The reactor temperature then was increased to 103° C., and 0.43 part of liquid PEVE was injected into the reactor. After the temperature had become steady at 103° C., HFP was added slowly to the reactor until the pressure was 350 psig (2.5 MPa). Then TFE was added to the reactor to achieve a final pressure of 600 psig (4.2 MPa). Then 0.86 part of a freshly prepared aqueous initiator solution containing 0.20 wt % of ammonium persulfate (APS) and 0.20 wt % potassium persulfate (KPS) was charged into the reactor at 0.11 part/min, thereby charging 0.0034 part of APS and KPS combined. Then, this same initiator solution was pumped into the reactor at 0.0074 part/min for the remainder of the polymerization. After polymerization had begun as indicated by a 10 psig (0.07 MPa) drop in reactor pressure, additional TFE was added to the reactor to maintain pressure constant at 600 psig (4.2 MPa) until a total of 17.5 parts of TFE had been added to the reactor after kickoff. Total reaction time was 175 min with a TFE addition rate of 0.1 part/min. The reaction rate was maintained constant by adjusting the agitator speed. At the end of the reaction period, the TFE feed and the initiator feed were stopped, and the reactor was cooled while maintaining agitation. When the temperature of the reactor contents reached 90° C., the reactor was slowly vented. After venting to nearly atmospheric pressure, the reactor was purged with nitrogen to remove residual monomer. Upon further cooling, the dispersion was discharged from the reactor at below 70° C. Solids content of the dispersion was 30.4 wt % and raw dispersion particle size (RDPS) was 0.174 µm. After mechanical coagulation, the polymer was isolated by compressing excess water from the wet polymer and then drying this polymer in a 150° C. convection air oven. The TFE/HFP/PEVE copolymer had an MV of $3.30 \times 10^3$ Pa·s, an HFPI of 2.53 (8.1 wt % HFP), a PEVE content of 1.45 wt %, and a melting point of 273° C. Total unstable fraction (TUF) for the raw polymer was only 0.08%, indicating good thermal stability. The total amount of initiator used for each mole of copolymer produced was only 0.20 mol/mol, based on polymer molecular weight calculated from MV as outlined above. A sample of this polymer was stabilized by heating at 360° C. for 1.5 hr in humid air containing 13 mol % water (humid heat treatment, HHT). Thereafter, TUF was 0.03%. Total weight loss across humid heat treatment was only 0.16%, consistent with the low TUF value for the unstabilized polymer. A film molded of stabilized copolymer resin then had an MIT Flex Life of 5300 cycles to break, showing the TFE/HFP copolymer made by the process of this invention to have good flex life despite relatively low HFP content.

Example 2

The procedure of Example 1 was essentially followed, except that 0.043 part of chloroform was used as CTA instead of ethane. Product properties are summarized in Table 1, along with those of Example 1 for reference. The notation "nc" indicates no change from Example 1. The data show that use of chloroform in the process of this also yields TFE/HFP copolymer having good flex life. TUF (0.13%) before HHT was low, as was weight loss across HHT, showing the overall stability of the copolymer made by the process of this invention. TFE/HFP copolymer resin in finely divided form as obtained by coagulation and drying was extruded to cubes using a 1-inch (2.54-cm) single-screw Haake extruder, with barrel temperature of 300° C. and die temperature of 340°–350° C., at a rate of 5 lb/hr (2.3 kg/hr). TUF of the product of this simple extrusion was a very low 0.02%.

Example 3

The procedure of Example 2 was essentially followed, except that the amount of choloroform was 0.0163 part and except for differences noted in Table 1. The notation "nc" indicates no change from Example 1 or 2. Product properties, also summarized in Table 1, show that a TFE/HFP copolymer having higher MV and greater flex life was made in this case.

TABLE 1

| Conditions and Results for Example 2 and Controls A-C | | | | | | |
|---|---|---|---|---|---|---|
| Example: | 1 | 2 | 3 | A | B | C |
| Run conditions: | | | | | | |
| Chain transfer agent | $C_2H_6$ | $CHCl_3$ | $CHCl_3$ | none | none | none |

TABLE 1-continued

Conditions and Results for Example 2 and Controls A-C

| Example: | 1 | 2 | 3 | A | B | C |
|---|---|---|---|---|---|---|
| PEVE precharge (part) | 0.43 | nc | 0.56 | nc | 0.44 | 0.26 |
| HFP pressure (MPa) | 2.5 | nc | nc | nc | nc | 3.0 |
| Initiator precharge (part) | 0.0034 | nc | 0.0033 | 0.0088 | 0.0095 | 0.0113 |
| Initiator solution pumping (part/min) | 0.0074 | nc | 0.013 | 0.042 | 0.044 | 0.048 |
| Dispersion properties: | | | | | | |
| Solids (wt %) | 30.4 | 30.3 | 30.2 | 31.7 | 28.3 | 31.2 |
| RDPS (μm) | 0.174 | 0.184 | 0.169 | 0.167 | 0.162 | 0.172 |
| Resin properties: | | | | | | |
| MV ($10^3$ Pa·s) | 3.30 | 4.00 | 7.4 | 2.40 | 2.40 | 2.23 |
| HFPI | 2.53 | 2.16 | 2.2 | 3.38 | 3.13 | 4.03 |
| HFP content (wt %) | 8.1 | 6.9 | 7.0 | 10.8 | 10.0 | 12.9 |
| PEVE content (wt %) | 1.45 | 1.44 | 1.72 | 1.08 | 1.23 | 0.79 |
| Melting point (°C.) | 273 | 280 | 269 | 258 | | |
| MIT Flex Life (cycles) | 5300 | 6240 | 27000 | 4400 | 2950 | 5770 |
| Initiator/polymer (mol/mol) | 0.20 | 0.21 | 0.28 | 0.78 | 0.83 | 0.87 |
| TUF before HHT (%) | 0.08 | 0.13 | 0.14 | 0.38 | 0.52 | 0.60 |
| TUF after HHT (%) | 0.03 | 0.02 | 0.07 | 0.02 | 0.01 | 0.05 |
| Weight loss across HHT (%) | 0.16 | 0.27 | 0.31 | 0.47 | 0.55 | 0.56 |
| —COOH before HHT (per $10^6$ C atom) | 330 | 215 | 174 | 630 | — | 750 |
| —COOH after HHT (per $10^6$ C atom) | 2 | 4 | — | 1 | 0 | 0 |

Controls A–C

The procedure of Example 1 was essentially followed, except for differences noted in Table 1. In particular, no CTA was used, and initiator precharge and pumping were higher. The notation "nc" indicates no change from Example 1. Product properties are also summarized in the Table. Higher TUF values before HHT, and higher weight losses across HHT, indicate lower overall stability than for TFE/HFP copolymers made by the process of this invention. The data also show higher unstable end group populations.

Example 4

Eleven batches of TFE/HFP copolymer were made by the general procedure of Example 2 except for adjustments in the amounts of CTA (chloroform), initiator precharge, and pumped initiator designed to obtain copolymer resin having lower MV. Relative to Example 2, CTA was increased by 92% and initiator precharge was increased by 28%. The amount of pumped initiator was varied somewhat over the laboratory campaign to adjust MV for blending purposes, resulting in an average increase in pumped initiator of 19%. Eight batches of raw dispersion were selected for blending in pairs, then were coagulated, dried, and extruded to conventional cubes (pellets) using a Werner & Pfleiderer Kombiplast® extruder (28 mm twin-screw followed by a single-screw extruder). No post-treatment, e.g., by elemental fluorine, was employed. Selected properties of the blended copolymer resin both before and after extrusion are given in Table 2.

TABLE 2

| Resin Properties for Multi-Batch Test | |
|---|---|
| Properties before extrusion: | |
| MV ($10^3$ Pa · s) | 2.04 |
| HFPI | 2.13 |
| HFP content (wt %) | 6.8 |
| PEVE content (wt %) | 1.35 |
| Melting point (°C.) | |

TABLE 2-continued

| Resin Properties for Multi-Batch Test | |
|---|---|
| MIT Flex Life (cycles) | 1500 |
| Initiator/polymer (mol/mol) | 0.20 |
| TUF before HHT (%) | 0.07 |
| TUF after HHT (%) | 0.00 |
| Weight loss across HHT (%) | 0.21 |
| Properties after extrusion: | |
| MV ($10^3$ Pa · s) | 1.85 |
| HFPI | 2.19 |
| HFP content (wt %) | 7.0 |
| PEVE content (wt %) | 1.34 |
| MIT Flex Life (cycles) | 1000 |
| TUF (%) | 0.04 |

Example 5

The TFE/HFP copolymer resin cubes prepared in Example 4 were used to extrude insulation onto AWG 24 solid copper conductor (20.1 mil=0.51 mm diameter), using a Nokia-Maillefer 60-mm extrusion wire line in a melt draw extrusion technique. The extruder had length/diameter ratio of 30/1 and was equipped with a conventional mixing screw (See Saxton, U.S. Pat. No. 3,006,029) to provide a uniform melt. Die diameter was 0.32 inch (8.13 mm), guide tip diameter was 0.19 inch (4.83 mm), and land length was 0.75 inch (19.1 mm). Cone length was 2 inch (51 mm) and the air gap to a water quench was 33 ft (10 m). The temperature profile, other running conditions, and results are shown in Table 3 for extrusions starting at 1500 ft/min (456 m/min) and increasing to 2700 ft/min (823 m/min) in 300 ft/min (91 m/min) increments. The absence of spark failures for extrusion speeds up to 2400 ft/min (732 m/min), for thin-walled (0.18 mm) insulation of resin prepared under laboratory handling conditions, indicates that TFE/HFP copolymer made by the process of this invention performed well.

TABLE 3

Extrusion Summary

| Temperatures (°F./°C.) | | | | | |
|---|---|---|---|---|---|
| Rear | ← 695/368 → | | | | |
| Center rear | ← 725/385 → | | | | |
| Center | ← 735/391 → | | | | |
| Center front | ← 735/391 → | | | | |
| Front | ← 740/393 → | | | | |
| Clamp | ← 740/393 → | | | | |
| Adapter | ← 740/393 → | | | | |
| Crosshead | ← 740/393 → | | | | |
| Die | ← 765/407 → | | | | |
| Melt | 755/ | 760/ | 762/ | 769/ | 771/ |
|  | 402 | 404 | 406 | 409 | 411 |
| Wire preheat | ← 280/138 → | | | | |
| Running conditions | | | | | |
| Wire speed (m/min) | 457 | 549 | 640 | 732 | 823 |
| Crosshead pressure (MPa) | 7.0 | 8.1 | 8.7 | 9.1 | 9.6 |
| Drawdown ratio | 84.3 | 84.3 | 85.1 | 85.8 | 82.9 |
| Extrudate properties | | | | | |
| Insulation diameter (mm) | 0.876 | 0.876 | 0.874 | 0.871 | 0.881 |
| Capacitance (pF/m) | 203 | 199 | 197 | 195 | 190 |
| Wire length coated (m) | 3658 | 3962 | 3962 | 3962 | 5486 |
| Spark failures | 1 | 0 | 0 | 0 | 15 |

I claim:

1. In the process of copolymerizing tetrafluoroethylene with hexafluoropropylene to form a partially crystalline copolymer having a total unstable fraction of at least 0.3%, said copolymerization being carried out in an aqueous medium in the presence of water soluble initiator, dispersing agent, and optionally chain transfer agent, the improvement comprising carrying out said copolymerization so as to produce said copolymer as polymerized having a total unstable fraction of no more than 0.2%, by (a) having the amount of said water soluble initiator present such that no more than half of the molecules of said copolymer made are initiated by said initiator, (b) having the amount of said chain transfer agent present such that chain transfer complements said initiator with respect to initiation of said copolymer molecules made, (c) having the amount of hexafluoropropylene present so as to counteract the reduction in copolymerization rate caused by (a) and (b), but also causing reduced toughness of said copolymer if this were the only change made to the copolymerization, the amount of hexafluoropropylene incorporated into said copolymer corresponding to HFPI of from 2.0 to 5.0, and (d) adding fluorinated vinyl ether to said aqueous medium for copolymerization with said tetrafluoroethylene and hexafluoropropylene, in an amount to compensate for the loss of toughness caused by insufficient hexafluoropropylene incorporated into said copolymer, the amount of fluorinated vinyl ether incorporated into said copolymer being from 0.2% to 4% by weight.

2. In the process of copolymerizing tetrafluoroethylene with hexafluoropropylene in an aqueous medium in the presence of water soluble initiator and dispersing agent to obtain a partially-crystalline copolymer of tetrafluoroethylene and hexafluoropropylene which has a total unstable fraction of at least 0.3%, the improvement comprising carrying out said copolymerizing wherein chain transfer agent is present, and said initiator is present in an amount effective to initiate no more than half of said copolymer molecules made, to obtain said copolymer as polymerized having a total unstable fraction of no more than 0.2%.

3. In the improved process of claim 2, wherein said copolymer comprises hexafluoropropylene in an amount corresponding to HFPI of from 2.0 to 5.0.

4. In the improved process of claim 3, wherein said copolymer further comprises from 0.2% to 4% by weight of at least one fluorinated vinyl ether.

5. An aqueous dispersion polymerization process for partially-crystalline copolymer comprising tetrafluoroethylene and hexafluoropropylene, said process comprising copolymerizing tetrafluoroethylene and hexafluoropropylene in an aqueous medium containing water soluble initiator and chain transfer agent, wherein no more than half of copolymer molecules made are initiated by said initiator, and wherein chain transfer complements said initiator with respect to initiation of said copolymer molecules made.

6. The process of claim 5, wherein said copolymer comprises hexafluoropropylene in an amount corresponding to HFPI of from 2.0 to 5.0.

7. The process of claim 6, wherein said copolymer further comprises from 0.2% to 4% by weight of at least one fluorinated vinyl ether.

8. The process of claim 5, wherein said copolymer as polymerized has total unstable fraction of no more than 0.2%.

9. The process of claim 5, wherein the amount of said water soluble initiator used is no more than 0.5 mole per mole of polymer made.

10. The process of claim 9, wherein the amount of said water soluble initiator used is no more than 0.35 mole per mole of polymer made.

11. In the process of claim 1 wherein the fluorinated vinyl ether has the formula $CF_2=CFOR$, wherein R is a fluorinated alkyl group containing from 1 to 8 carbon atoms.

12. In the process of claim 11 wherein said fluorinated vinyl ether is perfluoro(methyl vinyl ether), perfluoro(ethyl vinyl ether) or perfluoro(propyl vinyl ether).

* * * * *